United States Patent
Nakagawa

[11] Patent Number: 5,140,979
[45] Date of Patent: Aug. 25, 1992

[54] MASSAGER

[75] Inventor: Hajime Nakagawa, Tokyo, Japan

[73] Assignee: Shin-Atsu-Shin Clinic, Inc., Tokyo, Japan

[21] Appl. No.: 449,782

[22] Filed: Dec. 12, 1989

[30] Foreign Application Priority Data

Dec. 12, 1988 [JP] Japan ................. 63-312100
Sep. 8, 1989 [JP] Japan ................. 1-231452

[51] Int. Cl.5 .................. A61H 23/00; A61H 1/00
[52] U.S. Cl. ................... 128/55; 128/421; 128/24.1; 128/24.5; 128/907
[58] Field of Search ............. 128/24.1, 24.5, 51, 128/52, 44, 60, 61, 54, 55, 735, 907, 242, 32, 67, 802, 421, 24 A, 422

[56] References Cited

U.S. PATENT DOCUMENTS

| 965,564 | 7/1900 | Coates | 128/67 |
|---|---|---|---|
| 3,626,934 | 2/1971 | Andis | 128/55 |
| 3,837,335 | 9/1974 | Teranishi | 128/52 |
| 4,016,873 | 4/1977 | Anderson | 128/54 |
| 4,079,733 | 3/1978 | Denton et al. | 128/55 |
| 4,088,128 | 5/1978 | Mabuchi | 128/52 |
| 4,198,963 | 4/1980 | Barkalow | 128/53 |
| 4,428,368 | 1/1984 | Torii | 128/38 |
| 4,513,737 | 4/1985 | Mabuchi | 128/52 |
| 4,549,535 | 10/1985 | Wing | 128/52 |
| 4,566,442 | 1/1986 | Mabuchi et al. | 128/52 |
| 4,741,347 | 5/1988 | Robert et al. | 128/800 |
| 4,763,657 | 8/1988 | Chen et al. | 128/67 |
| 4,827,914 | 5/1989 | Kamazawa | 128/51 |

FOREIGN PATENT DOCUMENTS

| 257989 | 3/1988 | European Pat. Off. | 128/802 |
|---|---|---|---|
| 544041 | 6/1922 | France | 128/60 |
| 2621827 | 4/1989 | France | 128/422 |
| 452530 | 10/1949 | Italy | 128/55 |
| 669897 | 4/1989 | Switzerland | 128/54 |

Primary Examiner—Edgar S. Burr
Assistant Examiner—Eric Raciti
Attorney, Agent, or Firm—Felfe & Lynch

[57] ABSTRACT

A massager for giving vibratory hits on a skin face. A multiplicity of stimulative projections each having an acute apex are provided on an impingement vibrating member impinging on the skin face. The impingement vibrating member is fitted with an ion electrode for energizing pointwise the minus ions on the skin face. The ion electrode is formed with an energizing projection, whereby the minus ions act pointwise on the skin face.

5 Claims, 1 Drawing Sheet

MASSAGER

BACKGROUND OF THE INVENTION

The present invention is directed to a massager capable of performing a medical treatment in combination with natural curing functions by exciting or restraining nerves while imparting vibratory stimuli to a diseased part, keiketsu (parts effective for acupuncture), keiraku (a circulatory and reactive system which links the keiketsu one another) of a person undergoing medical treatment.

There have heretofore been practiced a variety of treating methods intended to perform medical treatments with the aid of natural curing functions by exciting or restraining the nerves. This involves an operation of giving physical stimuli to particular parts of a human body, i.e., so-called tsubo (vital parts) such as keiketsu and keiraku.

One typical example is an acupuncturing method in which the stimuli are given by acupuncturing the human body's particular parts, viz., the vital parts including keiketsu and keiraku. Based on this acupuncturing method, a human body is stuck inwards with a metallic needle composed of gold, silver, iron and the like, thus stimulating the nerves. This stimulation in turn excites or restrains the nerves pertaining to a diseased part, with the result that natural curing functions inherent in the human body are activated to heal the diseased part.

A skin stimulating therapeutical appliance and a magnetic therapeutical appliance, which are employed in the acupuncturing method, are disclosed in, e.g., Japanese Utility Model Laid-Open Publication Nos. 56-81722, 58-115241 and 60-34841. Each of these therapeutical appliances includes a head provided, at its top end, with a stimulative member equipped with a single piece or a plurality of metallic needles. The diseased part is stuck with the head in such a manner that the diseased part undergoes a series of hits of the head which is inserted thereinto and retracted therefrom.

There arise, however, the following problems peculiar to the prior art therapeutical appliances. There is a probability that the metallic needle with which the human body is pricked tends to be corroded in the form of rust because of a nature inherent in the needle. Since the needle tip is pointed, it is dangerous to deal with the needle. Besides, the human body is pricked with the needle, and hence there exists a possibility that a treated person would be indirectly infected with pathogenic bacteria viruses or the like. Such a treatment has the small margin of safety Minus (negative) ions exist in interiors of well-conditioned cells of the human body, whereas plus (positive) ions encircle cell exteriors. In this state, the cells are metabolized. In the reversed condition, the cell interiors assume the plus ions, and the exteriors thereof assume the minus ions. Under such a reversed condition, the cells are not metabolized but fatigued, resulting in deterioration thereof. In addition, a relatively oft-happened electrifying phenomenon associated with the plus ions of the cells of the human body can be seen in the above-described vital parts or the like. As a result, this causes functional declines of tissues and multiple organs of the human body and further, it can be recognized, exerts malign influences on the human body wherein chronic diseases are germinated.

The conventional therapeutical appliances are, however, confined to the function to mechanically stimulate the human body, so that it is in some cases difficult to exhibit fundamental medical effects, unless the electrified plus ions are eliminated.

SUMMARY OF THE INVENTION

It is a primary object of the present invention, which is devised under the aforementioned circumstances incidental to the prior art, to provide a massager capable of recovering natural healing power while exhibiting the exciting or restraining action on the nerves of a diseased part, keiketsu and keiraku of a treated person by giving mechanical stimuli to skin faces of these parts with a multiplicity of stimulative projections each having a substantially acute apex. It is another object of this invention to remove pains and other symptoms of the diseased part, this entailing a step of activating the cells by energizing pointwise the minus ions.

To accomplish the foregoing objects, according to one aspect of the invention, there is provided a massager for giving vibratory hits on a skin face, comprising an impingement vibrating member vibratingly impinging upon the skin face while moving to and fro, and a multiplicity of stimulative projections formed on a front surface of the impingement vibrating member and each having a substantially acute apex.

The stimulative projections each assuming a substantially quadrangular pyramidal shape may be arrayed on the front surface of the impingement vibrating member.

According to another aspect of the invention, there is provided a massager characterized by an impingement vibrating member fitted with an ion electrode for energizing pointwise the minus ions on the skin face.

According to still another aspect of the invention, there is provided a massager comprising an impingement vibrating member moving to and fro with respect to the skin face, a multiplicity of stimulative projections formed on the front surface of the impingement vibrating member and each having a substantially acute apex, an ion electrode, fitted to the underside of the impingement vibrating member, for energizing pointwise minus ions on the skin faces, and an energizing projection extending from a front surface of the ion electrode, the energizing projection jetting out of an outside hole perforated in a substantially central portion of the impingement vibrating member so as to penetrate the front surface of the impingement vibrating member.

The massager according to the present invention is arranged such that the impingement vibrating member moving to and fro with respect to the skin face is made to impinge on a diseased part of a person undergoing a medical treatment, and the stimulative projections of the impingement vibrating member give vibratory stimuli to the skin face of the diseased part, thus massaging it.

The diseased part and a variety of vital parts such as keiketsu and keiraku in the diseased part are vibratingly stimulated by the stimulative projections, and nerves associated therewith are excited or restrained to make the nerve activities sound, thus activating the natural curing functions.

On the other hand, the ion electrode impinging on the skin face acts to neutralize the plus ions electrified in the diseased part by energizing the minus ions therein. Besides, the diseased part itself is electrified with the minus ions to activate metabolisms of respective cells of the diseased part. The cells are thus brought into a sound state.

The energizing projection of the ion electrode which extends into the front surface of the impingement vibrating member serves to concentrate the pointwise energizing actions of the minus ions on the diseased part, thereby making effective the electrifying action on the minus ions.

BRIEF DESCRIPTION OF THE DRAWINGS

Other objects and advantages of the invention will become apparent during the following discussion taken in conjunction with the accompanying drawings, in which:

FIG. 1 is a partially cut-away side view;

FIG. 2 is a front elevation depicting a head; and

FIG. 3 is a partially cut-away side view illustrating the head.

DESCRIPTION OF THE PREFERRED EMBODIMENT

Figure 1:
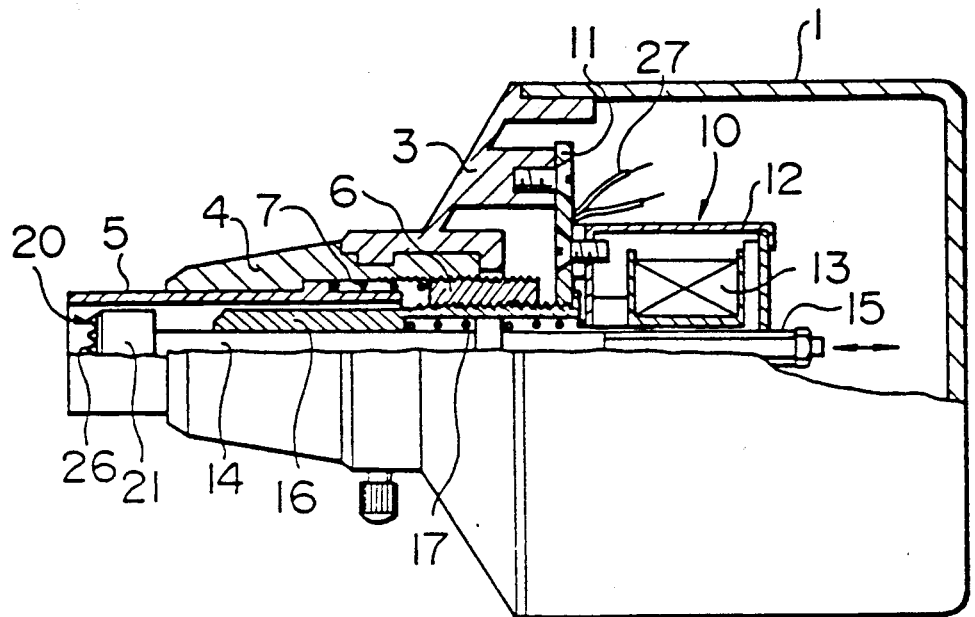
FIGS. 1 to 3 in combination show one embodiment of the present invention.
Figure 2:
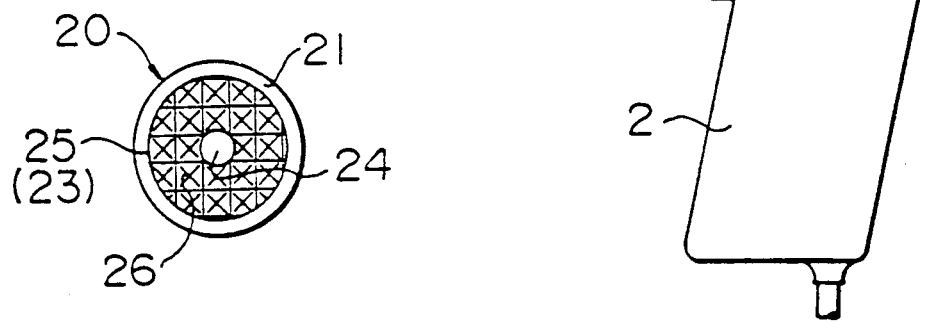
Figure 3:
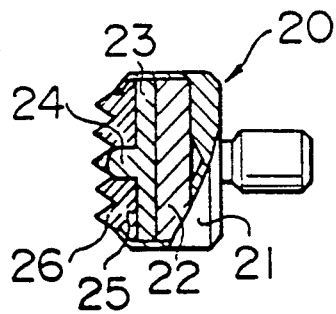

One embodiment of the present invention will hereinafter be described with reference to the accompanying drawings.

Designated at 1 in the Figures is a substantially cylindrical case which encases a vibrating mechanism 10. The case 1 is fitted with a handle 2, which is in turn mounted with a switch connected to a predetermined power source. Driving of the vibrating mechanism 10 is controlled by this switch.

Fixed to an opening portion formed in the front of the case 1 is a front cover 3 to which a head guide retaining member 4 formed in a substantially cylindrical shape is fixed. The head guide retaining member 4 accommodates a head guide 5 so retained by this member 4 as to be advanceable and retreatable.

The head guide 5 advances and retreats with the help of a resilient force of a coil spring 7 which is, as depicted in FIG. 1, contractibly interposed between a front end face of a fixing cylindrical member 6 fixed to a rear portion of the head guide retaining member 4 and a protruded portion shaped on a rear periphery of the head guide 5. When pushing backwards a top end of the head guide 5, the head guide 5 itself moves back resisting the resilient force of the spring 7. Upon release of the pushing force, the head guide 5 returns to a front position.

When the head guide 5 is retreated, a head 20, which will be mentioned later, is protruded outside from the top end of the head guide 5. The vibrating head 20 stimulates a skin face of a person who undergoes a medical treatment, at which time the top end of the head guide 5 is adapted to encircle a stimulative point.

The vibrating mechanism 10 is fixedly disposed onto a rear surface of a fixed base 11 fixed to a rear portion of the front cover 3. Namely, an arrangement of the vibrating mechanism 10 is such that a shaft 14 penetrates the center of an intermittently excited solenoid 13 incorporated in a coil case 12, and an iron core 15 fixed to a rear portion of the shaft 14 is magnetically attracted by the solenoid 13. Further, the shaft 14 passes through a bearing pipe 16 fixed to the front surface of the fixed base 11. Coil springs 17 are contractibly provided between front and rear surfaces of an annular shoulder formed on the outer periphery of the shaft 14, a stepped surface formed inwardly of the bearing pipe 16, and the front surface of the coil case 12.

The solenoid 13 is intermittently excited. During the excitation, the shaft 14 is moved back by magnetic attraction thereof through the iron core 15. Whereas during non-excitation, the shaft 14 is returned forward by the springs 17. A predetermined number of these operations are repeated during a given period, thereby moving the shaft back and forth with short strokes.

Fastened through a screw or other fixing means to the tip of the shaft 14 making the to-and-fro movements is the head 20 which is made to impinge on the skin face of the diseased part of the treated person.

The head 20 has its rear surface from which an external thread is protruded and its front portion formed with a head holder 21 including a recessed circular accommodation part. A magnet collar 22 is disposed innermost in the accommodation part, an ion electrode 23 is positioned in front of this magnet collar 22, and an impingement vibrating member 25 (a pyramid module) is placed in front of the ion electrode 23. An energizing projection 24 exposed from the front surface of the impingement vibrating member 25 is protrusively shaped on a front surface of a disc-like body of the ion electrode 23. Arrayed on the front surface of the impingement vibrating member 25 are a multiplicity of stimulative projections 26 each assuming a substantially quadrangular pyramidal shape to have a substantially acute apex. The energizing projection 24 in the central portion of the impingement vibrating member 25 is extended into the front surface of the impingement vibrating member 25 itself. In some cases, an apex of the stimulative projection 26 extending outwardly of the front surface of the impingement vibrating member 25 is slightly protruded from the front surface of the head 20.

Ions are supplied to the ion electrode 23 via the fixed base 11 connected to a lead wire 27 leading to an ion power source (not illustrated), the bearing pipe 16, the shaft 14 and the head guide retaining member 4. The supply of minus ions to the ion electrode 23 is not, as a matter of course, limited to the above-described route. A direct supplying route can be adopted for the arrangement.

Note that the impingement vibrating member 25 is integrally formed of a synthetic resin or the like by, e.g., extrusion molding. The material thereof is not, however, limited to the synthetic resin, and the front surface of the impingement vibrating member 25 is formed with as many stimulative projections 26 as possible.

The illustrated stimulative projection is formed to assume the substantially quadrangular pyramidal shape. The configuration thereof may, however, be modified with other conical or pyramidal shapes, for instance, conical or polygonal pyramidal configurations. The apexes are, as the case may be, slightly round. A mode of arrangement is arbitrary, wherein the stimulative projections 26 are not necessarily arrayed in vertical and crosswise directions. In short, each apex of the multiplicity of stimulative projections 26 is substantially acute to provide pointwise stimulating effects on the skin of the treated person.

One example of utilization of the massager will hereinafter be described. When the vibrating mechanism 10 is actuated by turning ON the power source, the head 20 mounted on the top end of the shaft 14 which moves to and fro with short strokes concurrently advances and retreats with the short strokes. In this manner, the impingement vibrating member 25 formed on the head 20 is made to impinge on the skin face of the diseased part of the treated person.

The stimulative projections 26 of the impingement vibrating member 25 give vibratory stimuli to the skin face of the diseased part, thus massaging this part. The vibratory stimuli at this time are concentrated on the diseased part and further a variety of vital parts including keiketsu and keiraku thereof. The nerves associated therewith are excited or restrained to make the nerve activities sound, thus activating the natural curing functions.

On the other hand, the energizing projection 24 formed on the ion electrode 23, which extends outwardly of the front surface of the impingement vibrating member 25, acts to effect pointwise energizing on the diseased part. Subsequently, the plus ions electrified in the diseased part are neutralized. Furthermore, the minus ions are electrified to activate the metabolisms of the various cells in the diseased part, thereby bringing the cells into a sound state.

As discussed above, in accordance with the present invention having the foregoing construction, there is exhibited the exciting or restraining action on the nerves pertaining to the diseased part, keiketsu, keiraku and the like of the treated person by mechanically stimulating the skin faces of these parts with the multiplicity of stimulative projections 26, thus recovering the natural healing power. The cells can be activated by addition of the minus ions which are energized pointwise by the ion electrode 23. The pains and other symptoms of the diseased part can be eliminated by synergism.

Namely, the typical arrangement of the invention is that the front surface of the impingement vibrating member 25, which vibratingly impinges on the skin face while moving to and fro, is formed with the multiplicity of the stimulative projections 26 each having the substantially acute apex. With this arrangement, the same effects as those in the moxibustion and acupuncture utilizing the conventional needles.

The stimulative projections 26 each assuming the substantially quadrangular pyramidal shape are arrayed on the front surface of the impingement vibrating member 25, whereby the to-and fro vibrations of the whole impingement vibrating member 25 exhibit secure massaging action on the skin face. Besides, the human body does not have to be stuck inwards with the needle, and hence the massager of the invention is sanitary, and there is little probability that the treated person be infected.

In addition, the ion electrode 23 fitted to the impingement vibrating member 25 serves to energize pointwise the minus ions on the skin face, thereby neutralizing the plus ions electrified in the diseased part and in turn electrifying the minus ions. Pointwise energizing of the minus ions on so-called tsubo (vital parts) such as keiketsu, keiraku and the like activate the various cells of those parts greatly contributes to eliminate the pains and other symptoms of the diseased part in combination with the activated metabolisms.

The impingement vibrating member 25 formed, on its front surface, with the multiplicity of stimulative projections 26 each having a substantially acute apex and the ion electrode 23 combined therewith cooperate to exhibit the above-described actions complexly. Highly adequate massaging effects are presented to recover the natural curing functions, thereby mitigating and removing pains and, so to speak, stiffened muscles.

In particular, since the energizing projection 24 formed on the front surface of the ion electrode 23 secured to the underside of the impingement vibrating member 25 is extended into the front surface of the impingement vibrating member 25 in the hole perforated in the substantially central portion thereof, the minus ions energized from the upper ends of the stimulative projections 26 act pointwise on the skin face, and concentrated pointwise energizing on the keiketsu, keiraku and the like thereby becomes effective. Where the impingement vibrating member 25 itself is composed of a synthetic resin, it is possible to converge pointwise energizing actions more effectively.

Although the illustrative embodiment of the present invention has been described in detail with reference with the accompanying drawings, it is to be understood that the invention is not limited to that precise embodiment. Various changes or modifications may be effected therein by one skilled in the art without departing from the scope or spirit of the invention.

What is claimed is:

1. A massager for giving vibratory hits on a skin face, comprising:
    an impingement vibrating member moving to and fro with respect to a skin face, said member having a hole perforated in a substantially central portion thereof;
    a multiplicity of stimulative projections formed on a front surface of said impingement vibrating member and each having a substantially acute apex; and
    an ion electrode, fitted to the underside of said impingement vibrating member, for energizing minus ions on the skin face, characterized in that an energizing portion projecting from a front surface of said ion electrode extends into said hole perforated in said impingement vibrating member.

2. The massager as set forth in claim 1, wherein said stimulative projections each assuming a substantially quadrangular pyramidal shape are arrayed on the front surface of said impingement vibrating member.

3. A massager as in claim 1 wherein said energizing portion is recessed below the apices on said front surface of said impingement vibrating member.

4. A massager as in claim 1 further comprising a tubular guide about said impingement vibrating member and spring means causing said guide to extend beyond said front surface of said impingement vibrating member, said guide being retractable against the force of said spring means when brought to bear against said skin face, thereby causing said front surface of said impingement vibrating member to contact said skin face.

5. The massage as in claim 1 wherein said energizing portion is recessed below the apices of the stimulative projections.

* * * * *

UNITED STATES PATENT AND TRADEMARK OFFICE
CERTIFICATE OF CORRECTION

PATENT NO. : 5,140,979

DATED : August 25, 1992

INVENTOR(S) : Hajime Nakagawa

It is certified that error appears in the above-identified patent and that said Letters Patent is hereby corrected as shown below:

Column 1, line 53 for "small" read -- smallest --.

Signed and Sealed this

Twelfth Day of October, 1993

Attest:

BRUCE LEHMAN

*Attesting Officer*   *Commissioner of Patents and Trademarks*